(12) United States Patent
Xiao et al.

(10) Patent No.: US 12,167,957 B2
(45) Date of Patent: Dec. 17, 2024

(54) STENT GRAFT

(71) Applicant: Shenzhen Lifetech Endovascular Medical Co., Ltd., Shenzhen (CN)

(72) Inventors: Benhao Xiao, Shenzhen (CN); Jiangfeng Tang, Shenzhen (CN); Caiping Liu, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 38 days.

(21) Appl. No.: 17/774,977

(22) PCT Filed: Dec. 1, 2020

(86) PCT No.: PCT/CN2020/133175
§ 371 (c)(1),
(2) Date: May 6, 2022

(87) PCT Pub. No.: WO2021/110001
PCT Pub. Date: Jun. 10, 2021

(65) Prior Publication Data
US 2022/0378571 A1 Dec. 1, 2022

(30) Foreign Application Priority Data
Dec. 3, 2019 (CN) .......................... 201911223422.4

(51) Int. Cl.
*A61F 2/07* (2013.01)
(52) U.S. Cl.
CPC .......... *A61F 2/07* (2013.01); *A61F 2002/072* (2013.01); *A61F 2220/0041* (2013.01); *A61F 2230/0019* (2013.01); *A61F 2250/0037* (2013.01)

(58) Field of Classification Search
CPC .................. A61F 2/07; A61F 2002/072; A61F 2230/0019; A61F 2250/0029;
(Continued)

(56) References Cited

U.S. PATENT DOCUMENTS 5,282,823 A * 2/1994 Schwartz .................. A61F 2/88
606/198
6,042,605 A * 3/2000 Martin ...................... A61F 2/07
623/1.13
(Continued)

FOREIGN PATENT DOCUMENTS

CN 101283937 A 10/2008
CN 102488575 A 6/2012
(Continued)

OTHER PUBLICATIONS

Canaud FR 3045312 translation (Year: 2017).*
(Continued)

*Primary Examiner* — Brian E Pellegrino
(74) *Attorney, Agent, or Firm* — Raymond Sun

(57) ABSTRACT

The present invention belongs to the field of medical devices, and specifically relates to a stent-graft. The stent-graft has a proximal greater curvature side and a proximal lesser curvature side. The stent-graft includes a stent body, an inner cover membrane disposed on the inner side of the stent body, and an outer cover membrane disposed on the outer side of the stent body. The stent body includes a plurality of wave rings axially arranged at intervals. Alternatively arranged crests and troughs are formed on the wave rings. The outer cover membrane is provided with a first opening, and the first opening exposes at least one trough located at or nearer to the proximal greater curvature side. According to the stent-graft of the embodiments of the present invention, the exposed trough can easily hang on a vessel wall, and thereby achieving the function of prevent- (Continued)

ing the stent-graft from shifting. The crests and troughs located at the proximal lesser curvature side of the stent-graft remain covered by the outer cover membrane. Therefore, the stack state of the cover membrane and the wave ring in a stent lumen is in the blood flow direction, thereby reducing the risk of thrombosis.

10 Claims, 11 Drawing Sheets

(58) Field of Classification Search
CPC .... A61F 2220/0008; A61F 2002/91525; A61F 2/915; A61F 2/2451; A61F 2/06; A61F 2250/0023; A61F 2250/0036
USPC ................................................ 623/1.16, 2.37
See application file for complete search history.

(56) References Cited

U.S. PATENT DOCUMENTS

| | | | |
|---|---|---|---|
| 6,533,807 B2 * | 3/2003 | Wolinsky ................ | A61F 2/966 623/1.18 |
| 7,186,264 B2 * | 3/2007 | Liddicoat .............. | A61F 2/2451 623/2.37 |
| 10,548,709 B2 | 2/2020 | Wang et al. | |
| 2009/0099650 A1 * | 4/2009 | Bolduc .................... | A61F 2/07 623/1.36 |
| 2009/0234433 A1 | 9/2009 | Richter | |
| 2017/0354521 A1 * | 12/2017 | Ryan ....................... | A61F 2/915 623/1.46 |
| 2020/0330215 A1 | 10/2020 | Xiao et al. | |

FOREIGN PATENT DOCUMENTS

| | | | | |
|---|---|---|---|---|
| CN | 104135966 | A | 11/2014 | |
| CN | 104434252 | A | 3/2015 | |
| CN | 104434352 | A | 3/2015 | |
| CN | 106344210 | | 1/2017 | |
| CN | 106344210 | A | 1/2017 | |
| CN | 107536658 | A | 1/2018 | |
| CN | 110393605 | A | 11/2019 | |
| CN | 110393607 | A | 11/2019 | |
| FR | 3045312 | A1 * | 6/2017 | ............... A61F 2/07 |
| WO | WO-0045741 | A1 * | 8/2000 | ............... A61F 2/07 |
| WO | WO-2019128703 | A1 * | 7/2019 | ............... A61F 2/07 |

OTHER PUBLICATIONS

Li et al. Covered Stent, translation of entire WO 2019/128703 document (Year: 2019).*
Office Action dated Sep. 28, 2021 for corresponding China Application No. 201911223422.4 (and Translation).
Response and Claims to Office Action dated Sep. 28, 2021 for corresponding China Application No. 201911223422.4 (and Translation).
Office Action dated Mar. 17, 2022 for corresponding China Application No. 201911223422.4 (and Translation).
Response to Office Action dated Mar. 17, 2022 for corresponding China Application No. 201911223422.4 (and Translation).
Notice of Grant dated Jun. 24, 2022 for corresponding China Application No. 201911223422.4 (and Translation).
International Search Report dated Feb. 18, 2021for corresponding PCT Application No. PCT/CN2020/133175.
Office Action for corresponding China Application No. 201911223422.4.
Search Report for corresponding China Application No. 201911223422.4.
Office Action dated Feb. 11, 2022 for corresponding India Application No. 202217035184.
European Search Report dated Nov. 30, 2023 in European Application No. EP 20 89 6721.

* cited by examiner

STENT GRAFT

TECHNICAL FIELD

The present invention belongs to the field of medical devices, and specifically relates to a stent-graft.

BACKGROUND ART

This section provides background information related to the disclosure only and is not necessarily the prior art.

Aortic stent-grafts are generally used for aortic interventional minimally invasive surgery to treat mainly aortic lesions such as aortic aneurysms and aortic dissections. Aortic stent-grafts can isolate the site of aortic lesions from the bloodstream so as to achieve proper cure. Existing aortic stent-grafts are mainly composed of a Nitinol metal stent and PTFE cover membrane. The PTFE cover membrane is divided into two layers, the inner and the outer, and the metal stent is encapsulated between the outer cover membrane and the inner cover membrane. The inner and the outer cover membranes are tightly fused together by a cover membrane heat treatment process at high temperature. In this type of stent-graft, since the metal stent is completely encapsulated by the PTFE membranes, the only portion of the stent-graft that directly contacts with the vessel wall is the outer PTFE membrane. The PTFE membrane is characterized by a very smooth surface. A smooth inner surface of the stent-graft makes thrombosis less likely to occur when blood flow passes through. However, a smooth outer surface of the stent-graft provides less friction so that the stent can more easily shift from its implanted position when it is attached to the inner surface of the vessel wall. Once the stent shifts, the procedure may fail.

As shown in FIG. 1, in order to reduce the risk of shifting of the stent-graft 200, it is common practice to use a narrow rectangular cover membrane 230 to form the outer cover membrane 20, so as to expose a portion of crests or troughs of the metal stent 10, thereby improving the anti-shifting performance of the stent. However, such a stent-graft 200 also has the following problems during use:

FIG. 2 shows one state of a conventional stent-graft (the outer cover membrane of which is not using a narrow rectangular cover membrane) 300 when it is bent. In the FIG., 1 is the greater curvature side (the side with a larger bending radius) of the stent, and 2 is the lesser curvature side (the side with a smaller bending radius) of the stent. When the stent-graft 300 is bent, the trough of the metal wave ring 311 on the metal stent 310 will upwarp relative to the side wall of the stent, and the upwarping direction is opposite to the direction in which the stent-graft 300 is bent. Viewed from the outside of the stent, on the lesser curvature side 2 of the stent, the troughs of the metal wave ring 311 are embedded to the inner side of the crests of the lower metal wave ring 311 (the side closer to the axis of the stent-graft is the inner side, and the side further away from the axis of the stent-graft is the outer side). Viewed from the lumen of stent, the stacking form of the cover membrane and the metal wave ring 311 at the lumen of the stent is that the troughs of the upper metal wave ring 311 cover the crests of the lower metal wave ring 311. Therefore, the stacking form of the cover membrane and the metal wave ring 311 at the lumen of stent is along the blood flow direction.

FIG. 3 shows the state of the stent-graft 200 with the outer cover membrane 20 using a narrow rectangular membrane 230 when the stent-graft 200 is bent; and when the stent-graft 200 is bent, the exposed trough of the metal wavy rings will upwarp. On the lesser curvature side 2 of the stent, the exposed troughs of the metal wave rings are blocked by the lower narrow strip cover membrane 230 when tilting upwardly. Therefore, when viewed from the outside of the stent, the troughs of the metal wave ring at the lesser curvature side 2 of the stent cover the crests of the lower metal wave rings. In this case, the stacking form of the cover membrane and the metal wave ring at the lumen of stent is reverse to the blood flow direction, which can easily result in thrombosis, and can also affect the patency of blood flow.

SUMMARY OF THE INVENTION

In view of the above problems, it is an object of the present invention to at least solve the problem of thrombosis at the bend that is experienced by the existing stent-graft having an outer membrane using a narrow rectangular membrane. This object is achieved through the following technical solution:

The embodiments of the present invention provide a stent-graft having a proximal greater curvature side and a proximal lesser curvature side. The stent-graft includes a stent body, an inner cover membrane disposed on the inner side of the stent body, and an outer cover membrane disposed on the outer side of the stent body. The stent body includes a plurality of wave rings arranged axially at intervals. Alternatively arranged crests and troughs are formed on the wave rings. The outer cover membrane is provided with a first opening, and the first opening exposes at least one trough located at or nearer to the proximal greater curvature side.

In some embodiments of the present invention, the first opening extends from the proximal lesser curvature side to the proximal greater curvature side, with the height of the first opening gradually increasing from the proximal lesser curvature side to the proximal greater curvature side. The first opening exposes a plurality of troughs located at or nearer to the proximal greater curvature side. Troughs located at the proximal lesser curvature side are all covered by the outer cover membrane.

In some embodiments of the present invention, the first opening is a circumferentially extending rectangular opening disposed on the proximal greater curvature side, the rectangular opening exposing a plurality of troughs on the same wave ring.

In some embodiments of the present invention, the length of the first opening in the circumferential direction is one third to two thirds of the length of the outer cover membrane in the circumferential direction.

In some embodiments of the present invention, there are a plurality of the first openings and they are distributed at and nearer to the proximal greater curvature side, with each of the first openings being a rectangular opening exposing one of the troughs.

In some embodiments of the present invention, there are a plurality of the first openings and they are distributed at and nearer to the proximal greater curvature side, with each of the first openings being a slit through which one of the troughs protrudes out of the outer cover membrane.

In some embodiments of the present invention, a second opening is further provided on the outer cover membrane. The second opening is nearer to a distal end of the stent body, and the second opening is a circumferentially extending and end-to-end annular opening. The second opening exposes all the crests on the same wave ring.

In some embodiments of the present invention, the stent-graft further includes a plurality of reinforcement wires arranged axially at intervals, each of the reinforcement wires being circumferentially wound around the stent body, and the reinforcement wires being positioned to avoid the first opening and the second opening.

In some embodiments of the present invention, the height of the exposed portion of the wave ring is no more than one third of the height of the wave ring.

In some embodiments of the present invention, for wave rings having at least a portion exposed, the screw rods on which the crests and troughs are connected are provided with arc-shaped transition sections.

The advantages of the present invention are that:

According to the stent-graft of the embodiments of the present invention, the outer cover membrane is provided with a first opening, and the first opening exposes at least one trough located at or nearer to the proximal greater curvature side; and the exposed trough can easily hang on a vessel wall, and thereby achieve the function of preventing the stent-graft from shifting. The crests and troughs located at the proximal lesser curvature side of the stent-graft remain covered by the outer cover membrane; the troughs of the wave ring at the proximal lesser curvature side are embedded to the inner side of the crests of the adjacent lower wave ring thereto. Viewed from the stent lumen, the stacking form of the cover membrane and the wave ring at the stent lumen is that the troughs of the upper wave ring cover the crests of the lower wave ring, so that the stack form of the cover membrane and the wave ring at the stent lumen is in the blood flow direction, thereby reducing the risk of thrombosis. In addition, when a conventional stent-graft uses a narrow rectangular cover membrane as the outer cover membrane, since the exposed portion of the metal stent is covered with only the inner cover membrane but lacks the outer cover membrane, it may cause an uneven thickness of the overall cover membrane and the risk of rupture at the position where the membrane thickness is thin. Compared with this stent-graft, the stent-graft of the embodiments of the present invention has relatively lesser exposure of the troughs through the first opening, and it can be understood that when the exposed area of the stent body is smaller, the area of the stent-graft having uneven thickness of the cover membrane is relatively reduced, so that the risk of rupture of the membrane is reduced.

BRIEF DESCRIPTION OF THE DRAWINGS

The drawings are only for purposes of illustrating the preferred implementations and are not to be construed as limiting the present invention. And throughout the drawings, like reference numerals represent like components. In the drawings.

DETAILED DESCRIPTION OF THE INVENTION

Figure 1:
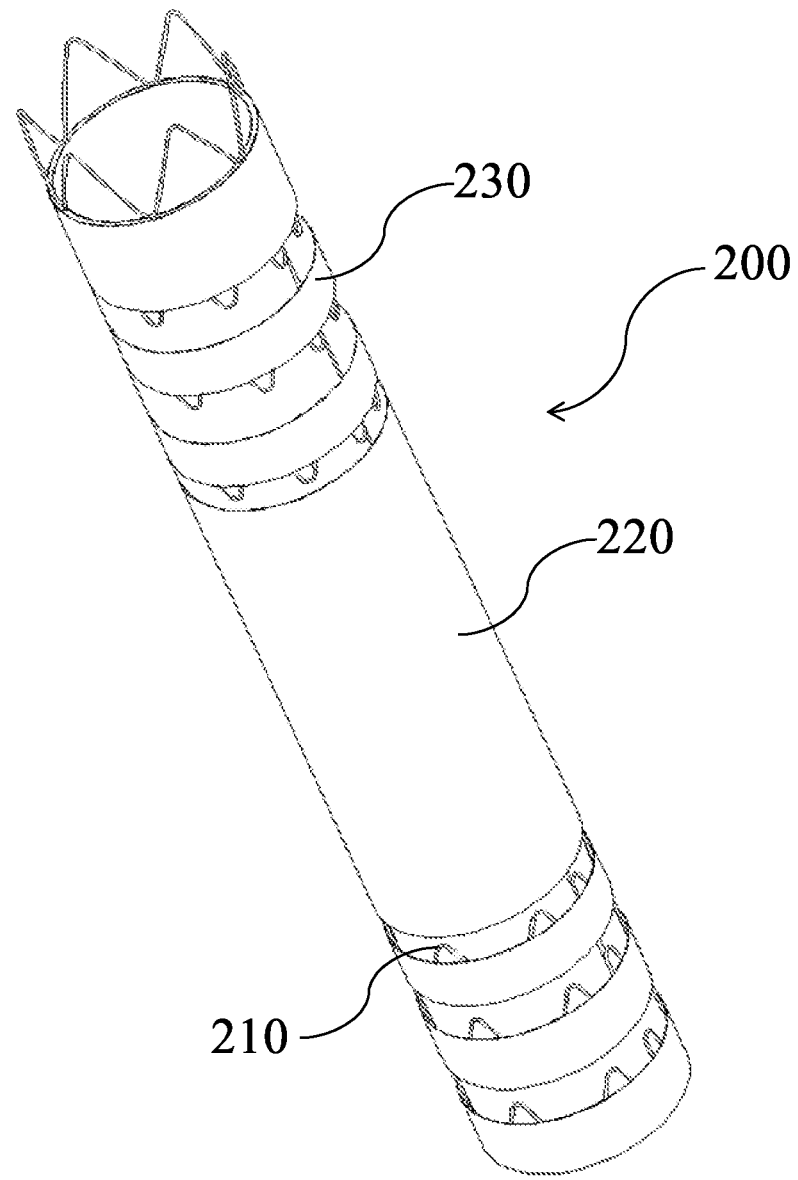
FIG. 1 is a schematic view of a stent-graft with an outer cover membrane using a narrow rectangular cover membrane in the prior art.
Figure 2:
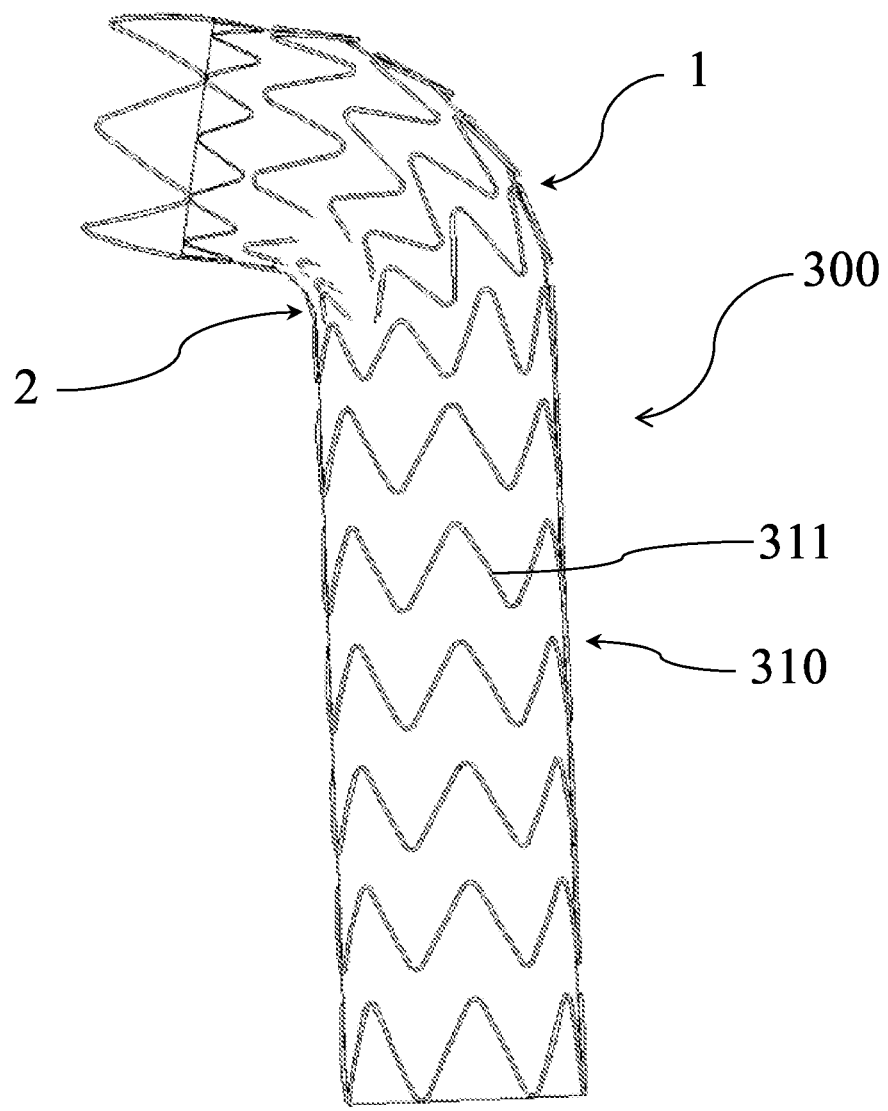
FIG. 2 is a schematic view of a conventional stent-graft in the prior art.
Figure 3:
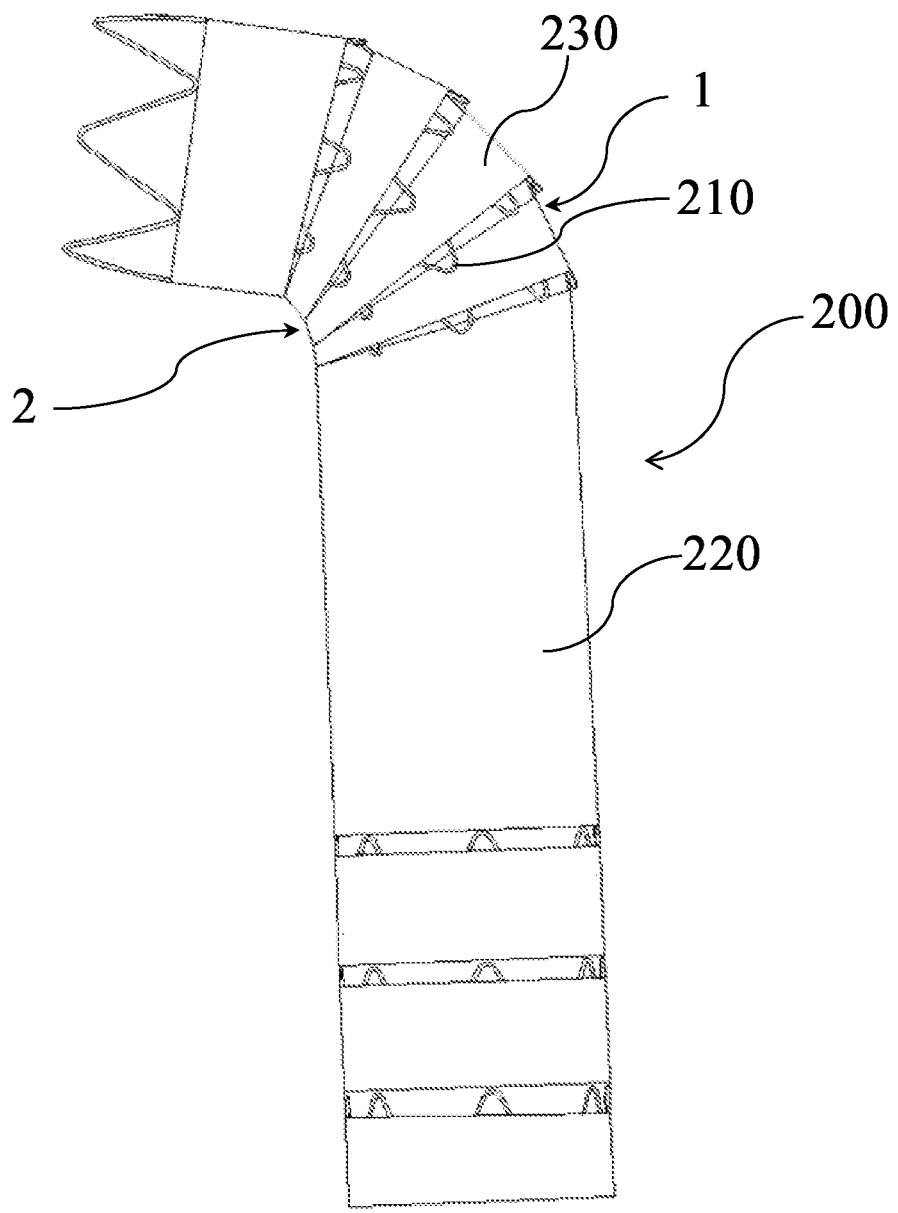
FIG. 3 is a schematic view of the stent-graft shown in FIG. 1 when bent.

Exemplary implementations of the present disclosure will be described in more detail below with reference to the accompanying drawings. Although the drawings show the exemplary implementations of the present disclosure, it should be understood that the present disclosure may be implemented in various forms and should not be limited to the implementations described herein. Instead, these implementations are provided such that the present disclosure can be understood more thoroughly, and can fully convey the scope of the present disclosure to those skilled in the art.

It should be understood that the terms used herein are for the purpose of describing specific exemplary implementations only, and are not intended to give any limitation. As used herein, the singular forms "a/an", "one" and "the" may also include plural forms, unless the context clearly indicates otherwise. The terms "comprise", "include", "contain" and "have" are inclusive, and indicate the existence of features, steps, operations, elements and/or components stated, but do not exclude the existence or addition of one or more other features, steps, operations, elements, components, and/or combinations thereof. The method steps, processes, and operations described herein are not to be construed as necessarily requiring them to be executed in the particular order described or illustrated, unless the order of execution is explicitly indicated. It should also be understood that additional or alternative steps may be used.

Although the terms first, second, third, etc., may be used herein to describe a plurality of elements, components, regions, layers and/or sections, these elements, components, regions, layers and/or sections should not be limited by these terms. These terms may be used solely to distinguish one element, component, region, layer or section from another region, layer or section. The terms such as "first", "second", and other numerical terms are not used to imply an order or sequence herein unless it is clearly indicated in the context. Thus, a first element, component, region, layer or section discussed below could be termed a second element, component, region, layer or section without departing from the teachings of the example implementations.

To facilitate description, spatially relative terms, such as "inside", "outside", "inner", "outer", "under", "below", "over", "above", may be used herein to describe the relationship of an element or feature relative to another element or feature as illustrated. Such spatially relative terms are intended to encompass different orientations of the device in use or in operation in addition to the orientations depicted in the drawings. For example, if a device in a drawing is turned over, elements described as "under other elements or features" or "below other elements or features" would then be oriented as "over other elements or features" or "above other elements or features". Thus, the example term "below" can encompass both an orientation of above and below. The device may be oriented otherwise (rotated by 90 degrees or in other directions) and will be interpreted by the spatially relative descriptors used herein accordingly.

In addition, when illustrating the implant, it is feasible to define the orientation according to the blood flow direction, and define that the blood flow flows from the proximal end to the distal end; for example, for the stent, it is defined in the present invention that the end where the blood flows in is "proximal end" and the end where the blood flows out is "distal end"; "axial" direction generally refers to the longitudinal direction of the stent as it is delivered.

Figure 4:
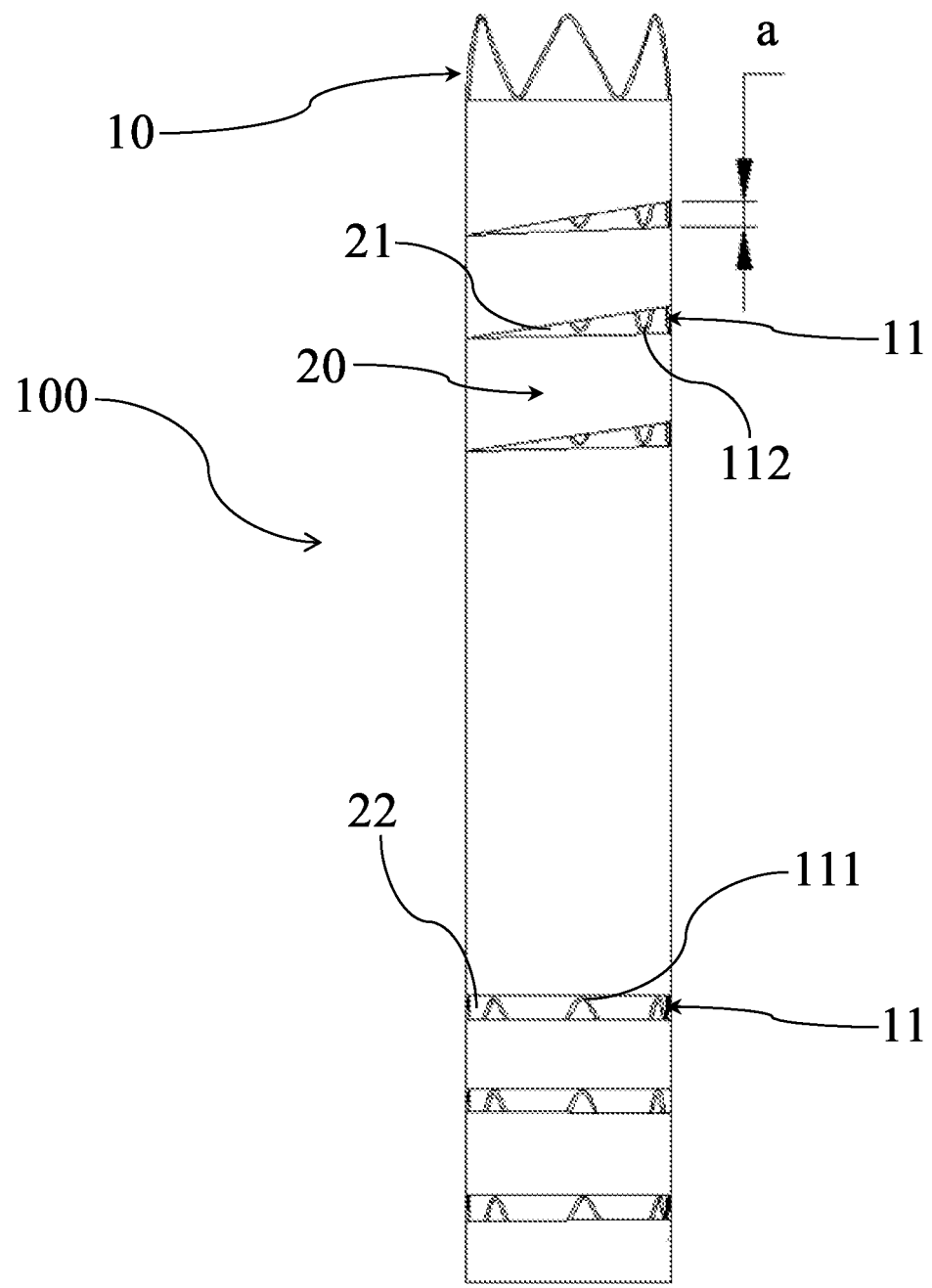
FIG. 4 is a schematic view of a stent-graft according to a first embodiment of the present invention.
Figure 5:
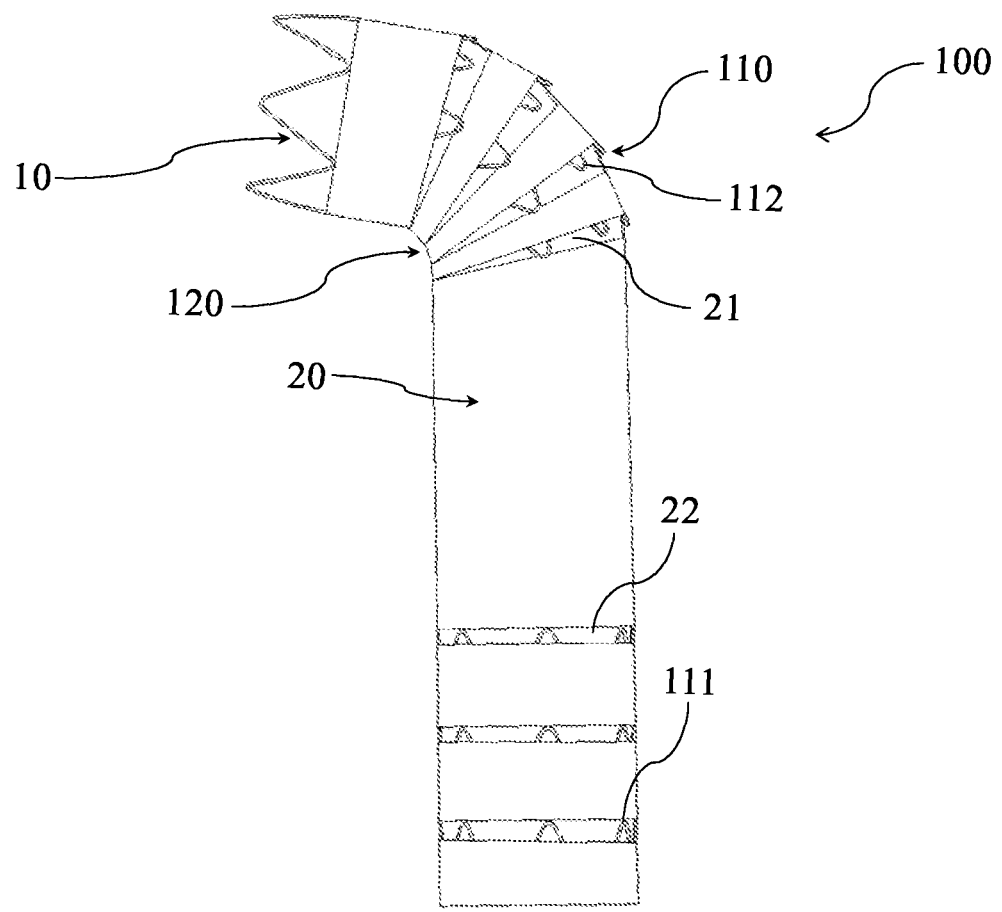
FIG. 5 is a schematic view of the stent-graft shown in FIG. 4 when bent.

As shown in FIGS. 4 and 5, a first embodiment of the present invention provides a stent-graft 100 having a proximal greater curvature side 110 and a proximal lesser curvature side 120, wherein the greater curvature side refers to the side with a larger bending radius and the lesser curvature side refers to the side with a smaller bending radius when the stent-graft 100 is bent after implantation in a blood vessel. Specifically, the stent-graft 100 includes a stent body 10, an inner cover membrane (not shown in the figure) disposed on the inner side of the stent body 10, and an outer cover membrane 20 disposed on the outer side of the stent body 10, wherein the stent body 10 includes a plurality of wave rings 11 arranged axially at intervals, and alternating arranged crests 111 and troughs 112 are formed on the wave rings 11, and the outer cover membrane 20 is provided with a first opening 21, and the first opening 21 exposes at least one trough 112 located at or nearer to the proximal greater curvature side 110.

It should be noted that, in the present invention, among the inflection points formed on the wave rings 11, the inflection point nearer to the proximal end of the stent-graft 100 is defined as a crest, and the inflection point nearer to the distal end of the stent-graft 100 is defined as a trough.

According to the stent-graft 100 according to one embodiment of the present invention, whose form is shown in FIG. 5 when it is implanted in the bend position of the thoracic aortic arch, the outer cover membrane 20 of the stent-graft 100 is provided with a first opening 21, and the first opening 21 exposes at least one trough 112 located at or nearer to the proximal greater curvature side 110. The exposed trough 112 can easily hang on a vessel wall, thereby achieving the function of preventing the stent-graft 100 from shifting. The crests and troughs located at the proximal lesser curvature side 120 of the stent-graft 100 remain covered by the outer cover membrane 20; and the troughs 112 of the wave ring 11 at the proximal lesser curvature side 120 are embedded to the inner side of the crests 111 of the lower wave ring 11 adjacent thereto. When viewed from the stent lumen, the stacking form of the cover membrane and wave ring of the stent lumen shows that the troughs 111 of the upper wave ring 11 cover the crests of the lower wave ring 11, so that the stack form of the cover membrane and the wave ring 11 at the stent lumen is in the blood flow direction, thereby reducing the risk of thrombosis.

In addition, when a stent-graft uses a narrow rectangular cover membrane as the outer cover membrane, since the exposed portion of the metal stent is covered with only the inner cover membrane but lacks the outer cover membrane, it may result in an uneven thickness of the overall cover membrane and there is a risk of rupture at the position where the membrane thickness is thin. Compared with this stent-graft, the stent-graft 100 of the embodiments of the present invention has relatively less exposure of the troughs 112 through the first opening 21, and it can be understood that when the exposed area of the stent body 10 is smaller, the area of the stent-graft 100 having uneven thickness of the cover membrane is relatively reduced, so that the risk of rupture of the membrane is reduced.

Further, the first opening 21 extends from the proximal lesser curvature side 120 to the proximal greater curvature side 110, with the height of the first opening 21 gradually increasing from the proximal lesser curvature side 120 to the proximal greater curvature side 110. The first opening 21 exposes a plurality of troughs 112 located at or nearer to the proximal greater curvature side 110. The troughs 112 located at the proximal lesser curvature side 120 are all covered by the outer cover membrane 20.

In the present embodiment, the first opening 21 extends from the proximal lesser curvature side 120 to the proximal greater curvature side 110, and the height of the first opening 21 gradually increases from the proximal lesser curvature side 120 to the proximal greater curvature side 110. Therefore, the first opening 21 may be formed by cutting the outer cover membrane 20 covering the stent body 10 along an oblique line, so as to expose the troughs 112 located at and nearer to the proximal greater curvature side 110. In addition, this way of forming the first opening 21 makes it possible to make the membrane at the proximal lesser curvature side 120 thicker and the membrane at the proximal greater curvature side 110 relatively thinner, thereby making it easier to bend the stent-graft 100 from the proximal greater curvature side 110 to the proximal lesser curvature side 120, and making the stent-graft 100 more flexible.

Further, there may be one or a plurality of the first openings 21, and when there are a plurality of the first openings 21, the plurality of the first openings 21 are arranged at intervals in the axial direction of the stent-graft 100. It can be understood that a greater number of first openings 21 may expose a greater number of wave rings 11 at the proximal end, and thus providing a better anchoring effect of the proximal end of the stent-graft 100 in the blood vessel.

Further, a second opening 22 is provided on the outer cover membrane 20. The second opening 22 is nearer to a distal end of the stent body 10, and the second opening 22 is a circumferentially extending and end-to-end annular opening. The second opening 22 exposes all the crests 111 on the same wave ring 11. The distal end of the stent-graft 100 is generally positioned in a straight section of the aortic vessel without significant bending. Therefore, the second opening 22 may be formed in such a way that exposes all the crests 111 of the entire wave ring 11. The second opening 22 is provided for exposing the crests 111 of the wave ring 11 nearer to the distal end of the stent-graft 100. The exposed crest 111 can easily hang on a vessel wall, thereby enhancing the anchoring force between the distal end of the stent-graft 100 and the blood vessel, thereby preventing the distal end of the stent-graft 100 from contracting proximally.

Further, there may be one or a plurality of the second openings 22, and when there are a plurality of the second openings 22, the plurality of the second openings 22 are arranged at intervals in the axial direction of the stent-graft 100. It can be understood that a greater number of second openings 22 may expose a greater number of wave rings 11 at the distal end, and thereby providing a better anchoring effect of the distal end of the stent-graft 100 in the blood vessel.

Further, the height a of the exposed portion of the wave ring 11 is no more than one third of the wave ring height c, i.e., a≤I/3c, wherein the wave ring height c refers to the dimension of the wave ring 11 in the axial direction of the stent-graft 100 and the height a refers to the dimension of the exposed portion of the wave ring 11 in the axial direction of the stent-graft 100. It can be understood that a greater height c of the exposed portion of the wave ring 11 may cause a smaller contact area between the unexposed portion and the outer cover membrane 20, resulting in an easy shifting of the metal wire constituting the wave ring 11 relative to the outer cover membrane 20. Therefore, limiting the height a of the exposed portion of the wave ring 11 to I/3c reduces the risk of the metal wire shifting relative to the outer cover membrane 20.

Figure 6:
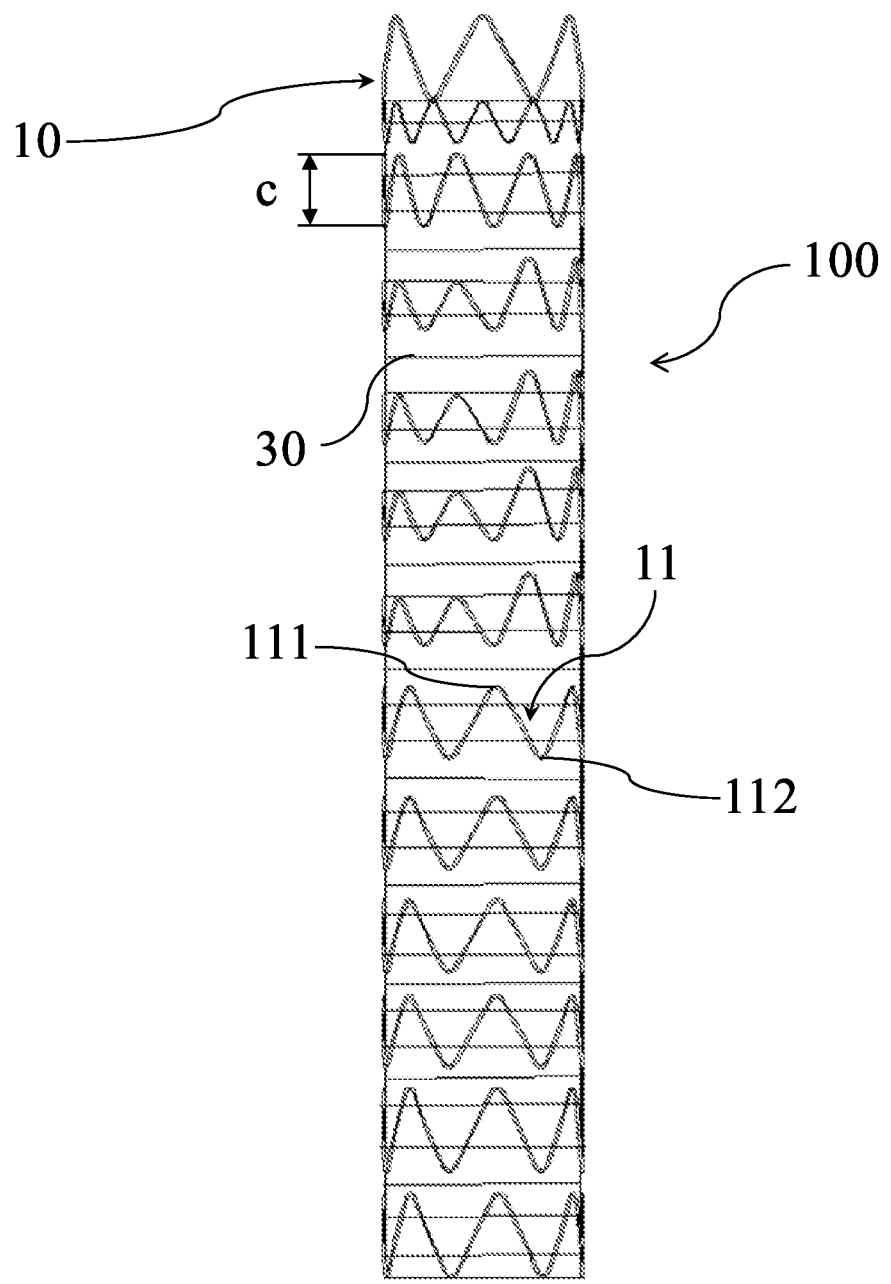
FIG. 6 is a schematic view of the stent-graft of the first embodiment of the present invention provided with reinforcement wires.

Further, as shown in FIG. 6, the stent-graft 100 further includes a plurality of reinforcement wires 30 axially arranged at intervals, each of the reinforcement wires 30 being circumferentially wound around the stent body 10, and the reinforcement wires 30 are provided so as to effectively reinforce the bonding force of the wave ring 11 with the outer cover membrane 20. Especially for the wave ring 11 having an exposed portion, the reinforcement wires 30 are beneficial to prevent the wave ring 11 from shifting relative to the outer cover membrane 20.

Further, the reinforcement wires 30 are disposed in a manner that avoids the first opening 21 and the second opening 22. Specifically, the reinforcement wire 30 may be maintained at a distance of 2 mm to 3 mm from the edge of the first opening 21 at a position nearer to the first opening 21 to ensure that the reinforcement wire 30 will not be exposed beyond the outer cover membrane 20 through the first opening 21. Similarly, the reinforcement wire 30 may be maintained at a distance of 2 mm to 3 mm from the edge of the second opening 22 at a position nearer to the second opening 22 to ensure that the reinforcement wire 30 will not be exposed beyond the outer cover membrane 20 through the second opening 22.

Further, the reinforcement wire 30 may be a PTFE wire, i.e., a wire made of PTFE material.

Figure 7:
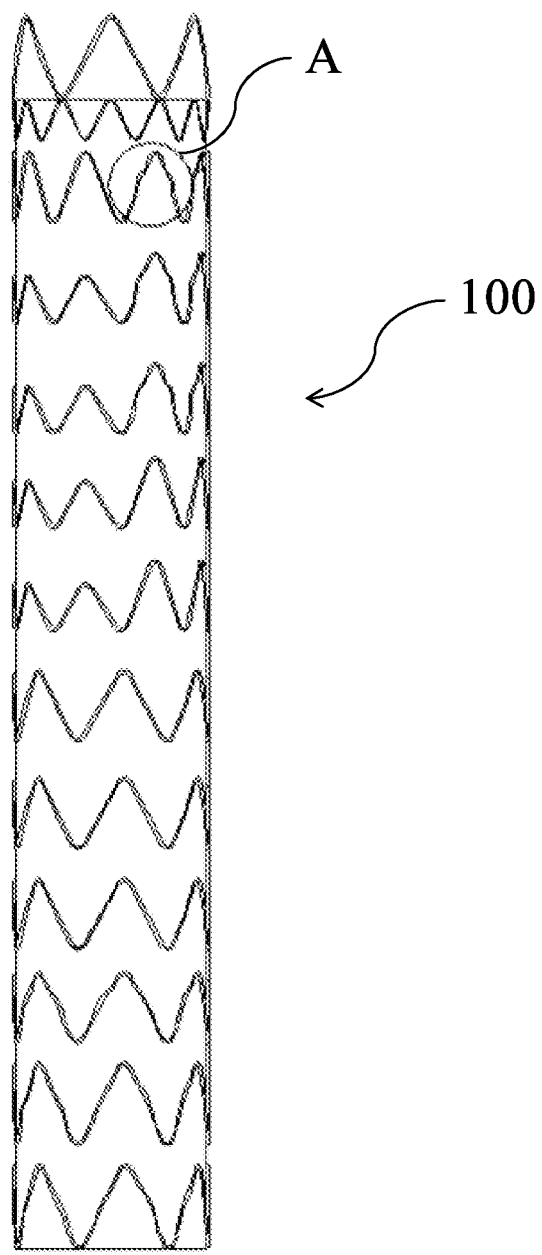
FIG. 7 is a schematic view of the stent-graft of the first embodiment of the present invention with arc-shaped transition sections being provided on the screw rod of the wave ring.
Figure 8:
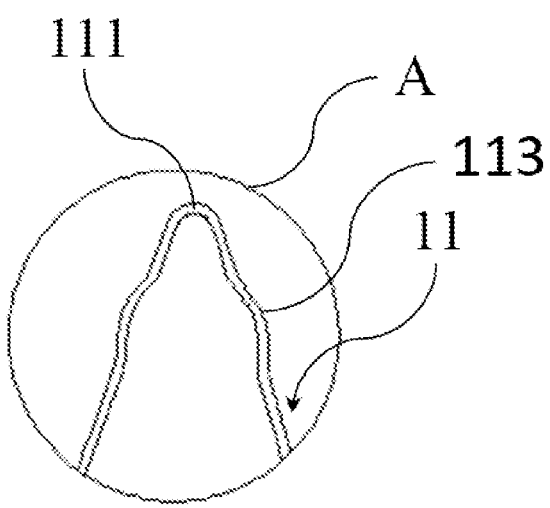
FIG. 8 is an enlarged view of the area A of FIG. 7.

Further, as shown in FIGS. 7 and 8, for wave rings 11 having at least a portion thereof exposed (including the wave ring 11 having trough 112 exposed at the proximal end and the wave ring 11 having crest 111 exposed at the distal end), the screw rods on which the crests and troughs are connected are provided with protrusions 113. In the present embodiment, each protrusion 113 is an arc-shaped transition section. For the wave ring 11, except for the crest 111 and trough 112, the other portions are straight transitions; after heat treatment of the cover membrane, since there is an exposed portion on the wave ring 11, after the metal wire is combined with the membrane, the force is along the direction of the straight section of the metal wire. Therefore, the force of the wave ring 11 against the shifting of the metal wire relative to the membrane is relatively small, which is easy to cause a shifting problem. In the present embodiment, the wave ring 11 having an exposed portion can be set as an arc section transition with a smaller curvature during heat-setting, thereby increasing the contact area between the metal wire and the cover membrane. In addition, after this structure is covered with the cover membrane, the force exerted by the metal wire on the inner and outer cover membrane is not along the longitudinal direction of the wire, but along the direction of the tangent of the arc section of the metal wire, so as to greatly improve the force against the shifting of the metal wire of the wave ring 11 and the cover membrane, and thereby reduce the risk of shifting between the wave ring 11 and the membrane. It can be understood that the arc-shaped transition sections in the present embodiment are not limited to being formed by braiding, but may be formed by cutting.

Figure 9:
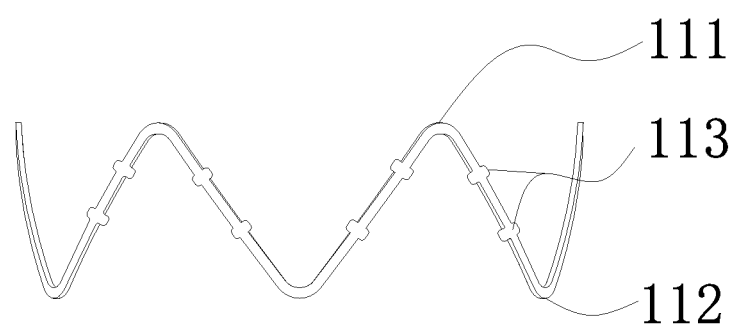
FIG. 9 is a schematic view of the stent-graft according to another embodiment of the present invention with protrusions being provided on the screw rod of the wave ring.

Further, as shown in FIG. 9, for wave rings 11 having at least a portion exposed (including the wave ring 11 having troughs 112 exposed at the proximal end and the wave ring 11 having crests 111 exposed at the distal end), the screw rod between the crest 111 and the trough 112 is provided with at least one protrusion 113. The protrusion 113 is used to increase the contact area between the metal wire and the cover membrane, so as to improve the bonding force between the metal wire and the cover membrane, and thereby reduce the risk of shifting of the wave ring 11 and the cover membrane. The shape of the protrusion 113 is not limited, as long as the contact area between the metal wire and the cover membrane can be increased. Specifically, the protrusion 113 is not limited to a ring shape, but may be an arc shape, a sphere shape, or the like. In the present embodiment, the specific shape of the protrusion 113 is formed by cutting.

Figure 10:
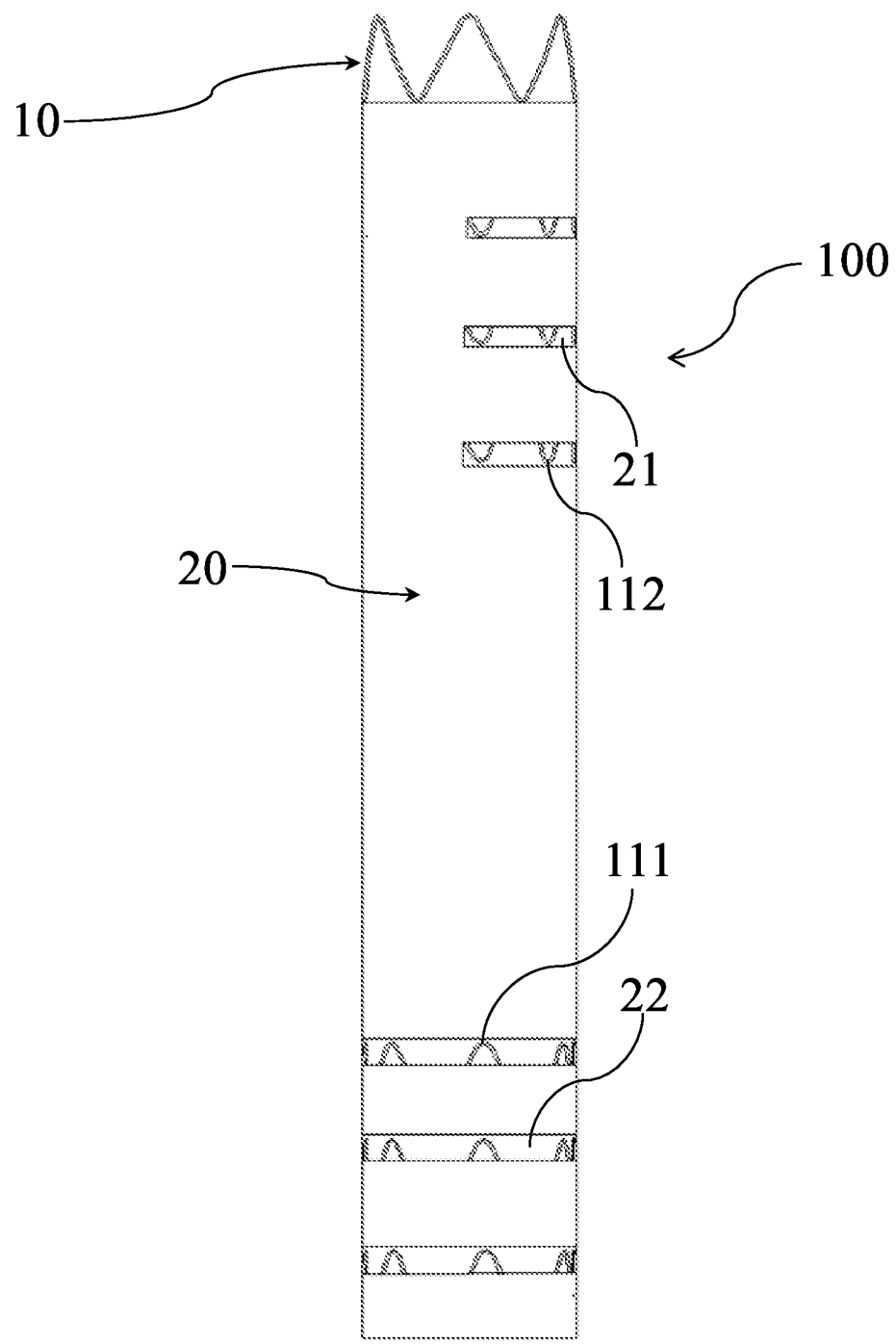
FIG. 10 is a schematic view of a stent-graft according a second embodiment of the present invention.

As shown in FIG. 10, a second embodiment of the present invention provides a stent-graft 100 having substantially the same structure as the first embodiment except that the shape of the first opening 21 is different.

Specifically, the second opening 21 is a circumferentially extending rectangular opening disposed on the proximal greater curvature side 110, the rectangular opening exposing a plurality of troughs 112 on the same wave ring 11. Thus, the troughs 112 at the proximal greater curvature side 110 may also be exposed, while the crests and troughs at the proximal lesser curvature side 120 remain covered by the outer cover membrane 20, thereby reducing the risk of thrombosis. In addition, the stent-graft 100 of the present embodiment can also provide an area which reduces the unevenness of the thickness of the cover membrane to a certain extent, thereby reducing the risk of membrane rupture.

Further, the length of the first opening 21 in the circumferential direction is one third to two thirds of the length of the outer cover membrane 20 in the circumferential direction, making it possible to obtain both a significant enhancement in the anchoring force of the proximal end of the stent-graft 100 to the blood vessel and an insignificant reduction in the force against shifting between the wave ring 11 and the outer cover membrane 20.

Figure 11:
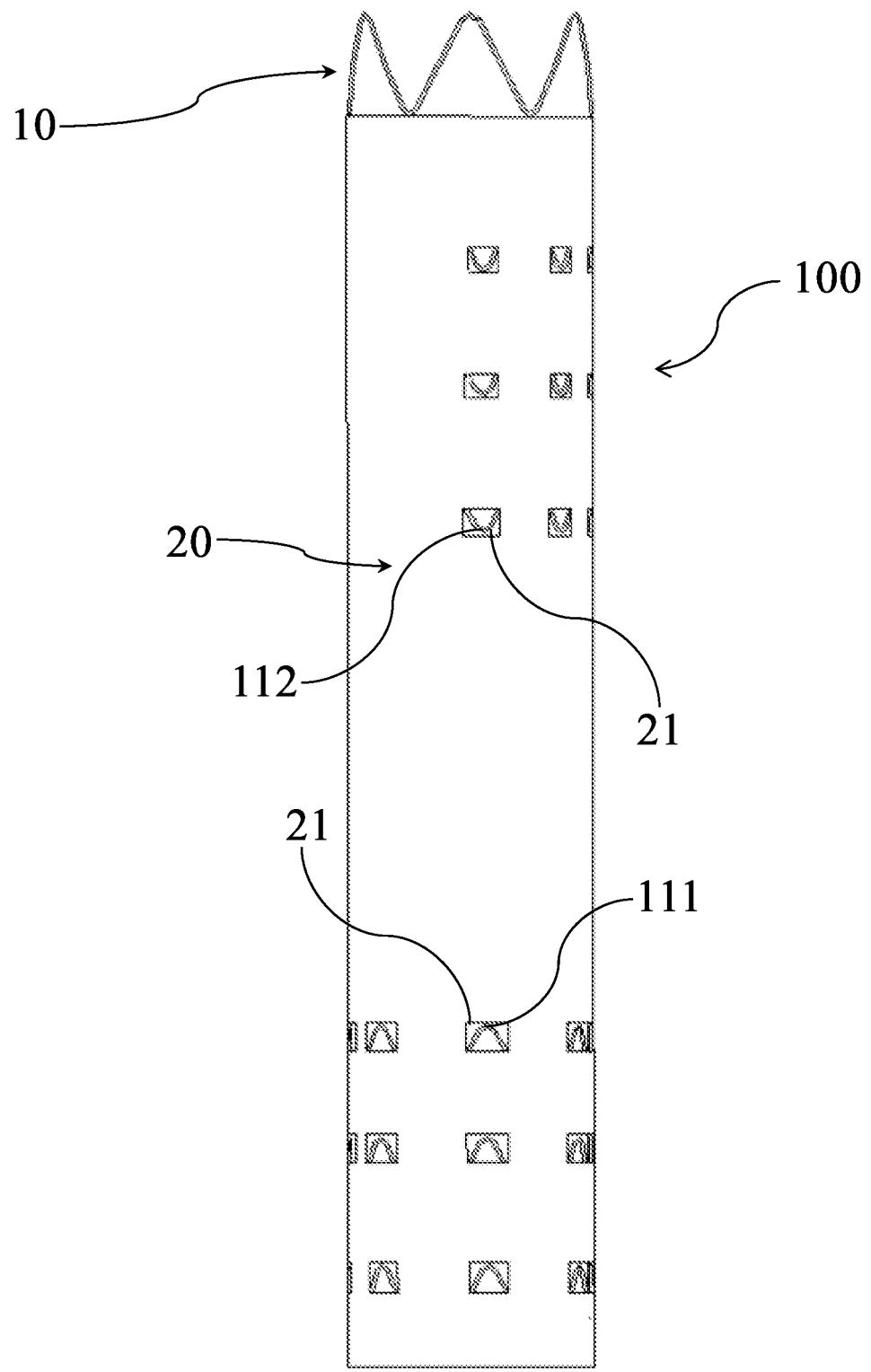
FIG. 11 is a schematic view of a stent-graft according to a third embodiment of the present invention.

As shown in FIG. 11, a third embodiment of the present invention provides a stent-graft 100 having substantially the same structure as the second embodiment except that the shape of the first opening 21 is different.

Specifically, there are a plurality of the first openings 21 and they are distributed along, and nearer to, the proximal greater curvature side 110, with each of the first openings 21 being a rectangular opening exposing one of the troughs 112. Compared with the second embodiment, the way of disposing the first opening 21 in this embodiment can further reduce the area of the portion of the stent body 10 that is not covered by the outer cover membrane 20, thereby further reducing the area of the stent-graft 100 having an uneven thickness of the cover membrane, thereby further reducing the risk of membrane rupture.

Figure 12:
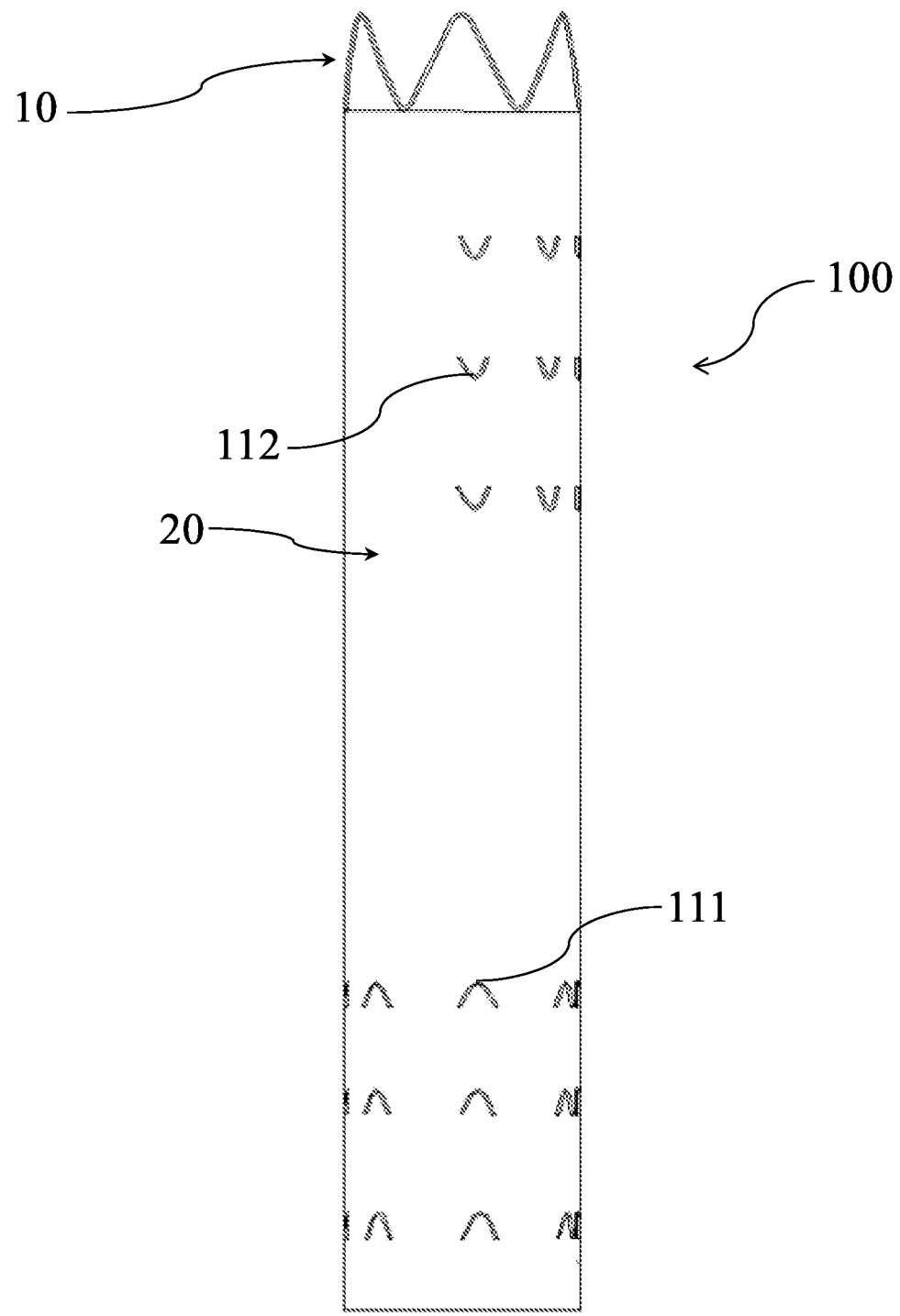
FIG. 12 is a schematic view of a stent-graft according to a fourth embodiment of the present invention.

As shown in FIG. 12, a fourth embodiment of the present invention provides a stent-graft 100 having substantially the same structure as the third embodiment except for further improving the form of the first opening 21.

Specifically, there are a plurality of the first openings 21 and they are distributed along and nearer to the proximal greater curvature side 110, with each of the first openings 21 being a slit through which one of the troughs 112 protrudes out of the outer cover membrane 20. Compared with the third embodiment, the first opening 21 in this embodiment is a slit, and the trough 112 protrudes out of the outer cover membrane 20 through the slit. In this way, the integrity of the outer cover membrane 20 can be ensured, so that the stent-graft 100 does not form uneven cover membrane thickness, thereby minimizing the risk of membrane rupture.

The above descriptions are merely better specific implementations of the present invention, but the protection scope of the present invention is not limited thereto. Any skilled person who is familiar with this art could readily think of variations or substitutions within the disclosed technical scope of the present invention, and these variations or substitutions shall fall within the protection scope of the present invention. Therefore, the protection scope of the present invention shall be subject to the protection scope of the claims.

The invention claimed is:

1. A stent-graft comprising: a stent body, an inner cover membrane disposed on an inner side of the stent body, and an outer cover membrane disposed on an outer side of the stent body, wherein the stent body comprises a plurality of wave rings arranged axially at intervals, with alternatively arranged crests and troughs formed on the wave rings, wherein the outer cover membrane is provided with at least one first opening located adjacent a proximal end of the stent body that has a varying height, and the first opening exposes a plurality of troughs;

wherein the first opening is formed by cutting the outer cover membrane along an oblique line such that the height of the first opening gradually increases circumferentially across the stent body from a first side which has no height to a second side which has the greatest height, the first opening exposing at least one trough of the plurality of troughs located at or nearer to the second side, and the troughs located at the first side are all covered by the outer cover membrane;

wherein at least one second opening is further provided on the outer cover membrane, the second opening is nearer to a distal end of the stent body, the second opening is a circumferentially extending annular opening, and the second opening exposes all the crests on the same wave ring; and wherein the stent-graft further comprises a plurality of reinforcement wires arranged axially at intervals in the axial direction of the stent graft length, each of the reinforcement wires being circumferentially wound around the stent body, and the reinforcement wires being positioned to avoid the first opening and the second opening;

characterized in that the reinforcement wires be maintained at a distance of 2 mm to 3 mm from the edge of the first opening, and the reinforcement wires be maintained at a distance of 2 mm to 3 mm from the edge of the second opening.

2. The stent-graft of claim 1, characterized in that the height of the exposed portion of the wave ring is no more than one third of the height of the wave ring.

3. The stent-graft of claim 1, characterized in that for the wave rings having at least a portion exposed, rods on which the crests and the troughs are connected are provided with protrusions.

4. The stent-graft of claim 1, characterized in that, the inner membrane covers the first opening in the inner side of the stent body.

5. The stent-graft of claim 1, characterized in that when the stent body is bent, the troughs of the wave ring at the first side are embedded to the inner side of the crests of the lower wave ring adjacent thereto.

6. The stent-graft of claim 1, characterized in that the inner cover membrane and the outer cover membrane are fused together.

7. The stent-graft of claim 1, wherein the inner cover membrane and the outer cover membrane define a combined thickness, and wherein the combined thickness in the first side is greater than the combined thickness in the second side.

8. The stent-graft of claim 1, characterized in that the reinforcement wires made of PTFE.

9. The stent-graft of claim 1, characterized in that the inner membrane covers the second opening in the inner side of the stent body.

10. The stent-graft of claim 1, characterized in that the first side and the second side are two sides which are contrary in radial direction.

* * * * *